United States Patent
Olek (10) Patent No.: US 10,294,527 B2
(45) Date of Patent: May 21, 2019

(54) EPIGENETIC MARKER FOR THE IDENTIFICATION OF NATURAL KILLER CELLS

(75) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 473 days.

(21) Appl. No.: 14/233,611

(22) PCT Filed: Jul. 23, 2012

(86) PCT No.: PCT/EP2012/064389
§ 371 (c)(1),
(2), (4) Date: Apr. 26, 2014

(87) PCT Pub. No.: WO2013/014122
PCT Pub. Date: Jan. 31, 2013

(65) Prior Publication Data
US 2014/0234837 A1    Aug. 21, 2014

(30) Foreign Application Priority Data

Jul. 22, 2011  (GB) .................................. 1112586.1

(51) Int. Cl.
*C12Q 1/68*    (2018.01)
*C12Q 1/6881*  (2018.01)
*C12Q 1/6883*  (2018.01)
*C12Q 1/6886*  (2018.01)

(52) U.S. Cl.
CPC ......... *C12Q 1/6881* (2013.01); *C12Q 1/6883* (2013.01); *C12Q 1/6886* (2013.01); *C12Q 2600/154* (2013.01)

(58) Field of Classification Search
None
See application file for complete search history.

(56) References Cited

FOREIGN PATENT DOCUMENTS

WO   WO 2010/125106 A1   11/2010

OTHER PUBLICATIONS

Baron, Udo et al., "DNA Methylation Analysis as a Tool for Cell Typing," *Epigenetics*, Jan./Feb./Mar. 2006, vol. 1, No. 1, p. 55-60.

Hanna, Jacob, and Mandelboim, Ofer, "The Real Function of NK Cells in vivo: When Killers Become Helpers," *Trends in Immunology*, 2007, vol. 28, No. 5, p. 201-206.

Higashimoto, Ken et al., "Characterization and Imprinting Status of OBPH1/obph1 Gene: Implications for an Extended Imprinting Domain in Human and Mouse," *Genomics*, Dec. 2002, vol. 80, No. 6, p. 575-584.

Li, Steven Shoei-Lung et al., "Epigenetic states and expression of imprinted genes in human embryonic stem cells," *World Journal of Stem Cells*, Aug. 26, 2010, vol. 2, No. 4, p. 97-102.

Walzer, Thierry et al., "Natural killer cells: from CD3⁻NKp46⁺ to post-genomics meta-analyses," *Current Opinion in Immunology*, 2007, vol. 19, p. 365-372.

*Primary Examiner* — Jehanne S Sitton
(74) *Attorney, Agent, or Firm* — Saliwanchik, Lloyd & Eisenschenk (57) ABSTRACT

The present invention relates to a method, in particular an in vitro method for identifying a subgroup of natural killer cells of a mammal, preferably CD3−, non T-lymphocyte derived NK cells, which often express the surface proteins CD56 and/or CD16, comprising analyzing the accessibility of the genomic DNA for OSBPL, such as OSBPL5, to bisulfite conversion and/or the methylation status of at least one CpG position in the genes for OSBPL, such as OSBPL5, in particular in their upstream and/or downstream regulatory regions, the promoter, introns, exons and introns exon borders and other conserved regions of said genes, wherein an increase of the accessibility of the genomic DNA and/or a demethylation in the sample as analyzed is indicative for said subgroup of NK cells. The analyses according to the invention can identify CD56+ cells and distinguish them from all other cells such as, for example, either CD56− and/or CD56 bright cells. The methods of the present invention are useful for the identification, the detection, the quantification and quality assurance and control of NK cells. Furthermore, the present invention relates to a kit for performing the above methods as well as respective uses of the inventive methods or kits. The present invention furthermore provides an improved method for analyzing the accessibility of the genomic DNA for OSBPL, such as OSBPL5, to bisulfite conversion and/or an analysis of the methylation status of at least one CpG position in the genes for OSBPL, such as OSBPL5, allowing for a precise analysis of both optimally and even from sub-optimal quality samples, such as non-freshly obtained blood, tissue or serum samples.

12 Claims, 3 Drawing Sheets
Specification includes a Sequence Listing.

Figure 1 a) Alignment of the amplicon AMP1746 with the genomic sequence (SEQ ID No. 2)

CTTCAAAAGTCATGGGCGAGGCTGGGCGGTGGCTCATGCCTGTAATCCCAGCACTTTGGGAGGCCGAGGCGGGCGGATCACCTG
AGGTCGGGAGTTCGAGATCAGCCTGACCAACATGGTGAAACCCTGTCTCTACTAAAAATACAAAATTAGCCAGGCGTGGTGGCGCA
TGCCTGTAATCCCAGCTACTTGGAGCCAAGATCACGCCATTGCACTCCAGCCTGGGCAACAAGAGCGAAACTCCATCTCAAAAAAA
AAAAAAAAAAGTCATGGGCAGATGAAGGCGAAGTAAAGATACCTTCAAGCAAATAACCAAAGGGTTTAGCATCTAGCTGCTCTCACAG
AGCCTGGCTCTGCCCTGCAGTGTGTGCTGAGCCTGAGCAGCGAGTTCCCTGCAGAGACAAGAGACAGCTCCTGGCACTTCCAGTGGTGTCTGTGCGTGAGTCAC
GAGCGTGGCTTTGCGCTGCCAGCAGCGCCGACAGCGAGTTCCCTGCAGAGACAAGAGACAGCAGTGAGTGCGGACAGCCCTTTCACATCTGAG
GCCACCCCTAAGTCACAGGGTCTGAGCTCCTTCCAACAGCTGAACACGCTCCTGGCACTTCCAGTGTGTCTGTGCGTGAGTCAC
TTAACCTCTCTGGGCCTCAGATTCTGTAAAATCCTGTCCAGTGTGCACAGGACATCTGTGCTGAGAAGTTATTTCACCTTTGACTTG
TTAGTGGTTTATTGCAGTCGCAAACTGCAGATTCGCAGGTTGCAGGGCTGCAAACTTTCAAACTCGACTGAGCCCTGCTCAGATT
TTAAACATCCCTGTGGAGGAGTACGCCTCGCTTGGGG b) AMP1746 sequence (SEQ ID No. 1)

ACCTTCAAACAAATAACCAAAAAATTTTAACATCTAACTACTCTCACAAAACCTAA
CTCTACCCTCGAAATATATAACTAAACCTCTCACCTTTACAATAAACGTAAAACAT
AATAAAATATAATCCTCGACTCGATTCAAAAAATAAAGTAACTTTACCGTCCA
ACAAGCCGACAACGAATTCCCTACAAAAAAACAAAAACAACAAAACCAATAAATA
CGAACAACCCTTTCACATCTAAA

SEQUENCE LISTING

<160> NUMBER OF SEQ ID NOS: 5

<210> SEQ ID NO 1
<211> LENGTH: 246
<212> TYPE: DNA
<213> ORGANISM: Homo sapiens

<400> SEQUENCE: 1
accttcaaac aaataaccaa aaaattttaa catctaacta ctctcacaaa acctaactct      60
accctcgaaa tatataacta aacctctcac ctttacaata aacgtaaaac ataataaaaa     120
tataatcctc gactcgattc aaaaaaataa acgtaactt  accgtccaac aacgccgaca     180
acgaattccc tacaaaaaca aaaaacaaca aaaccaataa atacgaacaa ccctttcaca     240
tctaaa                                                                246

<210> SEQ ID NO 2
<211> LENGTH: 846
<212> TYPE: DNA
<213> ORGANISM: Homo sapiens

<400> SEQUENCE: 2
cttcaaaagt catgggcgag gctgggcgcg gtggctcatg cctgtaatcc cagcactttg      60
ggaggccgag gcgggcggat cacctgaggt cgggagttcg agatcagcct gaccaacatg     120
gtgaaaccct gtctctacta aaaatacaaa attagccagg cgtggtggcg catgcctgta     180
atcccagcta cttggagcca agatcacgcc attgcactcc agcctgggca acaagagcga     240
aactccatct caaaaaaaaa aaaaaaaaaa gtcatgggca gatgaaggcg aagtaaagat     300
accttcaagc aaataaccaa agggttttag catctagctg ctctcacaga gcctggctct     360
gccctcggag tgtgtggctg agcctctcac cttgtcagtg ggcgtagggc atggtaaggg     420
tgtaatcctc ggctcggttc aggaaggtga gcgtggcttt gccgtccagc agcgccgaca     480
gcgagttccc tgcagagaca agagacagca ggaccagtga gtgcggacag ccctttcaca     540
tctgaggcca cccctaagtc acagggtctg agctccttcc aacagctgaa acgctcctg      600
gcacttccag tggtgtgtct gtgcgtgagt cacttaacct ctctgggcct cagattctgt     660
aaaatccttg tccagtgtgc acaggacatc tgtgctgaga agttatttca cctttgactt     720
gttagtggtt tattgcagtc gcaaaactgc agattcgcag ggtggaggct gcaaacttt      780
tcaaactcga ctgagccctg ctcagatttt aaacatccct gtggagggag tacgcctcgc     840
ttgggg                                                                846

<210> SEQ ID NO 3
<211> LENGTH: 22
<212> TYPE: DNA
<213> ORGANISM: Homo sapiens

<400> SEQUENCE: 3
taaaaatata atcctcgact cg                                               22

<210> SEQ ID NO 4
<211> LENGTH: 20
<212> TYPE: DNA
<213> ORGANISM: Homo sapiens

<400> SEQUENCE: 4
cgacaacgaa ttccctacaa                                                  20

```
<210> SEQ ID NO 5
<211> LENGTH: 29
<212> TYPE: DNA
<213> ORGANISM: Homo sapiens

<400> SEQUENCE: 5
ataaacgtaa ctttaccgtc caacaacgc                                    29
```

EPIGENETIC MARKER FOR THE IDENTIFICATION OF NATURAL KILLER CELLS

CROSS REFERENCE TO A RELATED APPLICATION

This application is a National Stage Application of International Application Number PCT/EP2012/064389, filed Jul. 23, 2012; which claims priority to Great Britain Application No. 1112586.1, filed Jul. 22, 2011; which are both incorporated herein by reference in their entirety.

The Sequence Listing for this application is labeled "SeqList-17Jan14.txt", which was created on Jan. 17, 2014, and is 3 KB. The entire content of the sequence listing is incorporated herein by reference in its entirety.

The present invention relates to a method, in particular an in vitro method for identifying natural killer cells and their subgroups in a mammal, preferably CD3 negative, non T-lymphocyte derived NK cells, which often express the surface proteins CD56 and/or CD16, comprising analyzing the accessibility of the genomic DNA for OSBPL, such as OSBPL5, to bisulfite conversion and/or the methylation status of at least one CpG position in the genes for OSBPL, such as OSBPL5, in particular in their upstream and/or downstream regulatory regions, the promoter, introns, exons and introns exon borders and other conserved regions of said genes, wherein an increase of the accessibility of the genomic DNA to chemical/other modifications and/or a demethylation in the sample as analyzed is indicative for said subgroup of NK cells. The analyses according to the invention can identify CD56$^+$ cells and distinguish them from all other cells such as, for example, either CD56$^-$ and/or CD56$^{bright}$ cells. The methods of the present invention are useful for the identification, the detection, the quantification and quality assurance and control of NK cells. Furthermore, the present invention relates to a kit for performing the above methods as well as respective uses of the inventive methods or kits. The present invention furthermore provides an improved method for analyzing the accessibility of the genomic DNA for OSBPL, such as OSBPL5, to chemical conversion, such as in particular by bisulfite treatment, and/or an analysis of the methylation status of at least one CpG position in the genes for OSBPL, such as OSBPL5, allowing for a precise analysis of both optimal quality samples, such as fresh (EDTA- or heparin or so) blood or fresh or fresh frozen tissue and even from suboptimal quality samples, such as non-freshly obtained, e.g. frozen blood, formalin fixed paraffin embedded tissue or frozen serum samples.

BACKGROUND OF THE INVENTION

Natural killer cells are cytotoxic lymphocytes, derived from CD34+ hematopoietic progenitor cells (HPCs). They represent an essential component of the innate immune system. They comprise about 2 to 20% of lymphocytes in the spleen, liver, and peripheral blood and are also present—even if potentially at lower frequencies—in other tissues such as bone marrow, thymus, lymph nodes, various organs and in various tissues of the body, either within the blood stream or infiltrated in the tissues. They were originally identified by their ability to kill certain (tumor-) target cells without sensitization. This killing works in vivo and in vitro and is not restricted by the target cell's expression of major histocompatibility complex (MHC) molecules. NK cells also possess natural cytotoxic activity against conspicuous, such as—but not restricted to (virus-) infected and/or tumor—cells. In addition, they mediate antibody-dependent cellular cytotoxicity (ADCC) of targets through Fc-gammaRIII (CD16), a receptor that binds the Fc portion of antibodies.

In general, the traditional identifier for human non-NKT NK cells is the absence of the T cell receptor complex (TCR, CD3), along with the expression of CD56, a 140-kDa isoform of neural cell adhesion molecule (NCAM). Based on their CD56 receptor expression density, human NK cells are often further subdivided into CD56$^{dim}$ or CD56$^{bright}$ NK cells. In the periphery, the majority (>90%) of NK cells have been found to consist of CD56$^{dim}$ along with high expression of CD16, and the remaining approximately 10% are CD56$^{bright}$ NK cells coming along with low or no expression of CD16.

The described CD56$^{dim}$ NK cell fraction is generally considered the "classical cytotoxic NK cell subset". The CD56$^{bright}$ fraction displays much lower cytotoxicity and, instead, produces high amounts of cytokines, including IFNγ and TNFα, indicating a primary role in immunoregulatory function. Hence, this fraction is sometimes referred to as regulatory NK cell fraction.

It is commonly thought that immune cell quantification is relatively easy and fully standardized, since the non-adherent, non-matrixed cells in peripheral blood can be marked with antibodies and flow-cytometrically quantitated. Providing that cells are non-adherent, single cell suspensions, intact and cell-type specific surface antigens are available, flow cytometry is indeed a highly accurate cell quantification tool.

However, for many applications in research and medical routine, the named prerequisites for such precise measurements are not given:

1. Often, the material/samples measured are not derived from peripheral blood and thus the solubility and single cell suspension property is not met. This is for example true for all biopsy analyzes, such as performed in the pathological routine.
2. Even if the analyte is peripheral blood, the prerequisite of having intact cells is difficult to meet, since—in order to maintain their structural integrity ("intactness")—these cells must not be frozen or stored as EDTA-blood for more than 6 hours, before subfractions, such as granulocytes start disintegrating.
3. In contrast to the common perception, there are not highly specific (surface) antigens for all immune cell types and hence the identification of cell types is not as unambiguous as may be hoped.
3a. Since antigen expression is not a digital process, thresholds must be defined to decide, whether cells belong to the positive or negative fraction. For NK cells, this problem is particular apparent:
As described above, NK cells are mainly defined by the expression of CD56 on their surface. For the identification of an NK cell type, this expression level is subdivided in three categories: CD56 negative, CD56dim and CD56 high. For none of these categories there is an independent, objective threshold. The three populations are always only identified and delimited based on their relative CD56 expression compared to the other fractions.

Hence, for many applications the current methodological approaches for a quantitative determination of immune cells remain problematic, such as for routine testing in clinical applications, which usually requires some lag times, and hence robustness and stability of the analyte. As said, the flow cytometric methods used for measurement of cells in peripheral blood are not adequate for immune cells infiltrating other tissues, including solid tissues during tumor development or at/after inflammation. Hence, flow cytometric methods are not applied in these areas and the surrogate methods (mostly immune histochemistry) are at most semi-quantitative methods.

The present inventors present a marker that can be used for the identification and quantification of NK cells in an alternative quantitative, more efficient, robust and integral approach: the analysis of cell type-, or cell status-specific epigenetic (DNA methylation and or chromatin structure and or DNA chemical inertness) markers. In the clinical routine and the general cell biological practice, the identification of specific epigenetic markers will greatly facilitate the measurement of blood and immune cell types.

For the purpose of definition for the present application, often, epigenetic variance in the DNA sequence is referred to by the terminology of DNA methylation. In the scientific literature, the status of methylation is often displayed as either "hyper" (above, more than normal, (lat.: super)) or "hypo" (below, less than normal, (lat.: sub) methylation. In the view of the inventor, these terms are inappropriate, since they suggest variance from the "normal" status. For healthy cells however, there is no such thing as non-normal, since for one cell type it is normal that it is methylated whereas the other is unmethylated. Both signatures are perfectly normal. For the inventor, gene regions are therefore either methylated or unmethylated (also and equivalent to unmethylated: demethylated). The potential decision as to whether a region in a cell type is aberrantly methylated (hypermethylated) or aberrantly demethylated (hypomethylated) may potentially play a role in certain diseases and decision may be made based on this. However, it is not an issue that is discussed or found in the technical process of measuring the methylation status in DNA. Despite this and owing to the general rules, whenever hypermethylation and hypomethylation is written it is thought to indicate the technical classification of demethylation and methylation.

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

The genes encoding members of the oxysterol-binding protein (OSBP) family are a group of intracellular lipid receptors that play a key role in the maintenance of cholesterol balance in the body. Most members contain an N-terminal pleckstrin homology domain and a highly conserved C-terminal OSBP-like sterol-binding domain. Transcript variants encoding different isoforms have been identified.

Accession number NG_009548 describes the 85237 bp DNA sequence of Homo sapiens oxysterol binding protein-like 5 (OSBPL5) on chromosome 11.

Li et al. (in: Li S S, Yu S L, Singh S. Epigenetic states and expression of imprinted genes in human embryonic stem cells. World J Stem Cells. 2010 Aug. 26; 2(4):97-102.) describe expression profiles of 32 known imprinted genes of five hESC lines. The expression levels of 21 imprinted genes were relatively low in undifferentiated hESC lines, and five of these genes (TP73, COPG2, OSBPL5, IGF2 and ATP10A) were found to be up-regulated in differentiated tissues.

Higashimoto et al. (in: Higashimoto K, et al., Characterization and imprinting status of OBPH1/Obph1 gene: implications for an extended imprinting domain in human and mouse. Genomics. 2002 December; 80(6):575-84.) describe the human 11p15.5, as well as its orthologous mouse 7F4/F5, imprinting domain. OBPH1 and Obph1 are located beyond the presumed imprinting boundary on the IPL/Ipl side. They determined full-length cDNAs and complete genomic structures of both orthologues and investigated their precise imprinting and methylation status. The orthologues resembled each other in genomic structure and in the position of the 5' CpG island and were expressed ubiquitously. OBPH1 and Obph1 were predominantly expressed from the maternal allele only in placenta, with hypo- and not differentially methylated 5' CpG islands in both species. These results suggested that the imprinting domain would extend beyond the presumed imprinting boundary and that methylation of the 5' CpG island was not associated with the imprinting status in either species. The publication does not disclose to use methylation analysis for the identification of cell types, and the genes are described as being expressed ubiquitously.

EP 1213360 describes a method of identifying a cell, tissue or nucleus, comprising collecting information on the methylation pattern of DNA isolated from the cell, tissue or nucleus and analyzing the resultant information.

WO 2004/050706 describes a sub-group of T-cells, and relates to characteristics of regulatory T-cells which define them as such. The application also describes the uses of such T-cells, compositions comprising them and chemokines which recruit them in the modulation of an immune response.

In view of the above, it is an object of the present invention to provide an improved method based on DNA methylation analysis as a superior tool in order to more conveniently and reliably identify and quantify NK cells and all different subsets of that cell type in a given sample derived/obtained from for example animal/human blood or tissue. Measurement can be done independent of purification, storage and to quite some extend also to tissue quality.

The importance of methylation becomes particularly apparent in tumor cells. Here, the "normal" methylation patterns—that are essential for a healthy development of a cell—are lost, and the cells therefore can no longer be controlled, and become not only epigenetically aberrant. Although aberrant methylation is not the primary subject of the present invention, the apparent significance of a correct epigenetic regulation becomes apparent by the close association between cancer cells and wrong methylation. Form this, one can conclude on the importance of a correct methylation. For single genes, as was shown earlier with the Foxp3 (Baron et al, Eur J Immunol. 2007 September; 37(9):2378-89; Wieczorek et al. Cancer Res. 2009 Jan. 15;

69(2):599-608) and CD3 locus (Sehouli et al. Epigenetics. 2011 Feb. 1; 6(2):236-46), the chemical/structural nature of the DNA at the given loci (such as the methylation status/imprint) coincides with the differentiation and the type of certain cells. This allows for an identification and quantification of the cell type of healthy cells based on their epigenetic fingerprint. In the present application this shall be achieved for healthy natural killer cells based on the genes for OSBPL, in particular for OSBPL5.

In a first aspect, the invention solves the above problem by providing a method for identifying natural killer cells ($CD56^{dim}$-cells and/or $CD56^{high}$ cells) in a sample derived from a mammal, comprising analyzing the methylation status and/or the accessibility to bisulfite conversion of at least one CpG position in one or more of the regions of the gene for oxysterol binding protein-like proteins (OSBPL), in particular for OSBPL5, wherein a demethylation of said at least one CpG position in said region as analyzed, when compared to an analogous position in a CD56 negative cell, is indicative for CD56 positive natural killer (NK) cell.

In a second aspect, the invention solves the above problem of identifying and quantifying classical $CD56^{dim}$ cells by providing a method for identifying $CD56^{dim}$ natural killer cells in a sample derived from a mammal, comprising analyzing the methylation status and/or the accessibility to bisulfite conversion of at least one CpG position in one or more of the regions of the gene for oxysterol binding protein-like proteins (OSBPL), in particular for OSBPL5, wherein a demethylation of said at least one CpG position in said region as analyzed, when compared to an analogous position in a non-NK-cell or a non-$CD56^{dim}$-NK cell, is indicative for a $CD56^{dim}$ natural killer cell.

In a preferred embodiment, said $CD56^{dim}$-natural killer cells of said mammal are CD3⁻ or CD3⁺.

Higashimoto et al. (in: Higashimoto K, Soejima H, Yatsuki H, Joh K, Uchiyama M, Obata Y, Ono R, Wang Y, Xin Z, Zhu X, Masuko S, Ishino F, Hatada I, Jinno Y, Iwasaka T, Katsuki T, Mukai T. Characterization and imprinting status of OBPH1/Obph1 gene: implications for an extended imprinting domain in human and mouse. Genomics. 2002 December; 80(6):575-84) describe that human 11p15.5, as well as its orthologous mouse 7F4/F5, is known as the imprinting domain extending from IPL/Ipl to H19. OBPH1 and Obph1 are located beyond the presumed imprinting boundary on the IPL/Ipl side. The orthologs resembled each other in genomic structure and in the position of the 5' CpG island and were expressed ubiquitously. OBPH1 and Pbph1 were predominantly expressed from the maternal allele only in placenta, with hypo- and not differentially methylated 5' CpG islands in both species. These results suggested that the imprinting domain would extend beyond the presumed imprinting boundary and that methylation of the 5' CpG island was not associated with the imprinting status in either species.

A further embodiment of the invention then comprises the inventive method, wherein said at least one CpG position is present in the 5' region upstream from the transcription start, promoter region, the 5' or 3' untranslated regions, intron, and/or exon/intron border, or in the 3' region downstream of the transcriptional stop.

A yet further embodiment of the invention then comprises the inventive method, wherein said at least one CpG position is selected from the CpG positions located in the amplicon OSBPL5 (Amp 1746) according to SEQ ID NO: 1, and preferably selected from positions 46, 66, 103, 130, 135, 152, 163, 173, 176, 182, or 224 of Amplicon No. 1746.

For a particular CpG as analyzed, theoretically there are four states per cell: (both alleles methylated), (allele A methylated, allele B unmethylated), (allele A unmethylated, allele B methylated), and (both alleles unmethylated). This leads to three different results: 100% methylated, 50% methylatedand 0% methylated. Thus, theoretically NK cells ($CD56^{dim}$) are 0% methylated, and non-NK cells (or $CD56^{bright}$ NK cells) are approximately 100% methylated. A similar situation is present for the assay analyzing the accessibility of the region as analyzed to bisulfite conversion, where NK cells ($CD56^{dim}$) are 0% accessible, and non-NK cells (or $CD56^{bright}$) are approximately 100% accessible. With OSBPL gene regions, 50% (de-) methylation was not observed in purified cell types but is possible to occur in two alternative scenarios:

1. Random methylation. In this case, regulatory function and association to either function or cell type is unlikely. Coincidentally, roughly 50% methylation may be observed in genes with "junk" methylation. This may be due to alternating and random methylation within one DNA strand or random methylation of one and random demethylation of the other DNA strand.
2. Principally, this 50% methylation can also occur in cell type/status specifically regulated genes. On one hand, imprinting or X-inactivation may lead to this. In this case, one allele is fully inactivated due to the requirement of a monoallelic gene expression. Hence, for genes that are monoallelically expressed but are still subject to cell specific regulation, one allele is switched (usually by epigenetic means) permanently and invariably throughout life whereas the other allele is switched on in selected cell types. With respect to the measurement, imprinting or X-inactivation are equivalent—the (from epigenetic measurement view less important) difference is solely that imprinted genes in all cells switch-off the same allele, whereas X-inactivation is mosaic.

In practical measurements employing e.g. bisulfite sequencing, the complete, "pure" methylation patterns are rarely detected, since both slight technical deficits of the employed technologies and possibly minor biological variances blur the theoretically expected values. Therefore, methods of the invention are preferred, wherein said at least one CpG position in said region as analyzed is demethylated to more than 80%, preferably more than 90%, and most preferred more than 95%, when compared to an analogous position in a non-NK cell.

Furthermore, the present invention includes methods, where more than one CpG position in a region is analyzed, such as, for example, 1, 2, 3, 4, 5, 6, 7, 8, 9, 10, or 11 positions (e.g. in the AMP 1746 region as above). Then, an overall methylation (or demethylation) of the region as analyzed can be determined, when compared to an analogous region in a non-NK cell. Therefore, also methods of the invention are preferred, wherein said region is demethylated (hypomethylated) to more than 70%, preferably more than 80%, or 90%, and most preferred more than 95% when compared to an analogous region (hyper or fully methylated) in a non-NK cell.

The person of skill will furthermore be able to select specific subsets of CpG positions in order to minimize the amount of sites to be analyzed, for example all sites as present on the amplicon according to SEQ ID No 1, or any other selected sub-sequence in the OSBPL genes as analyzed, for example as described above of the 5' region upstream from the transcription start, promoter region, the 5' or 3' untranslated regions, intron, and/or exon/intron border, or in the 3' region downstream of the transcriptional stop.

Yet another aspect relates to a method according to the present invention, wherein the analysis of the accessibility to bisulfite conversion and/or the methylation status comprises a method selected from methylation specific enzymatic digests, bisulphite sequencing, analysis selected from promoter methylation, CpG island methylation, MSP, HeavyMethyl, MethyLight, Ms-SNuPE, qPCR or other methods relying on the detection of genomic DNA, chemically or enzymatically modified DNA or amplified genomic or chemically or enzymatically modified DNA. Also preferred is an additional analysis of the marker CD56, CD16 and/or CD8.

Figure 2:
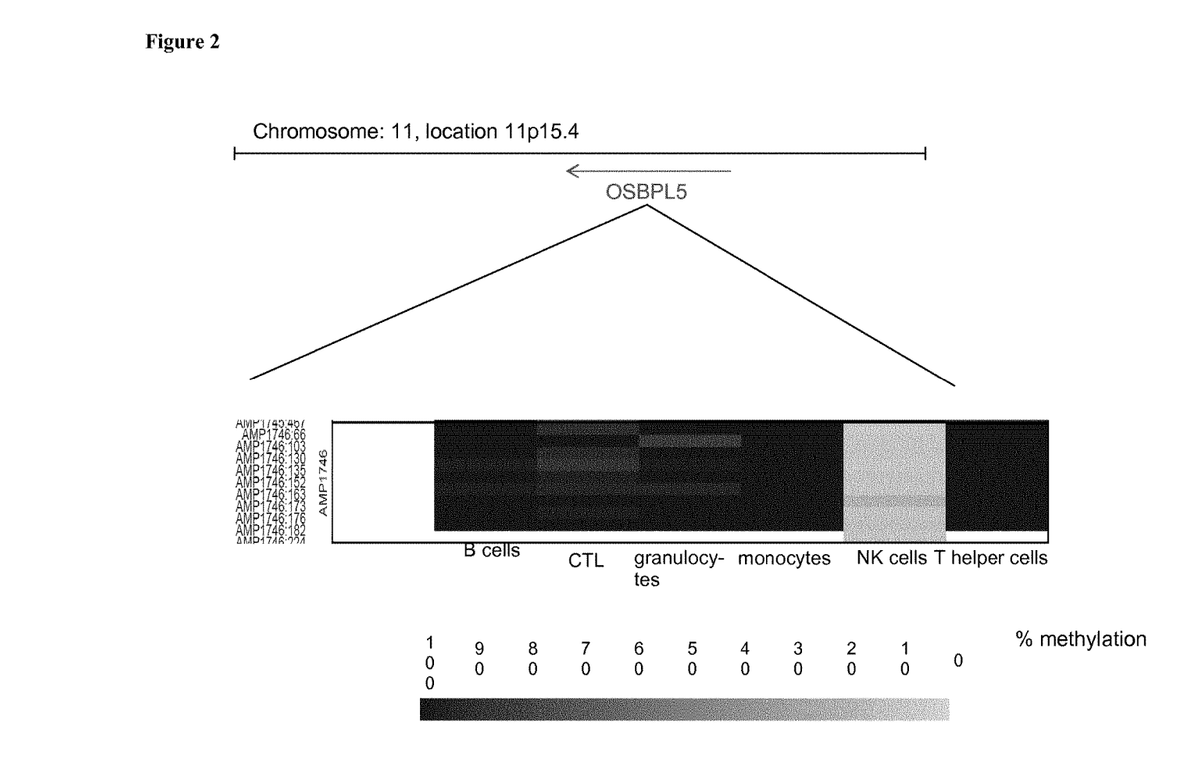
FIG. 2 shows the bisulfite conversion and sequencing of the OSBPL5 (AMP 1746, see FIG. 1) locus in different blood cell subtypes. The positions as analyzed from top to bottom are: 46, 66, 103, 130, 135, 152, 163, 173, 176, 182, and 224, respectively. The gray codes indicate the level of methylation in each cell type with dark gray representing full methylation and light gray indicating heavily decreased methylation.
Figure 3:
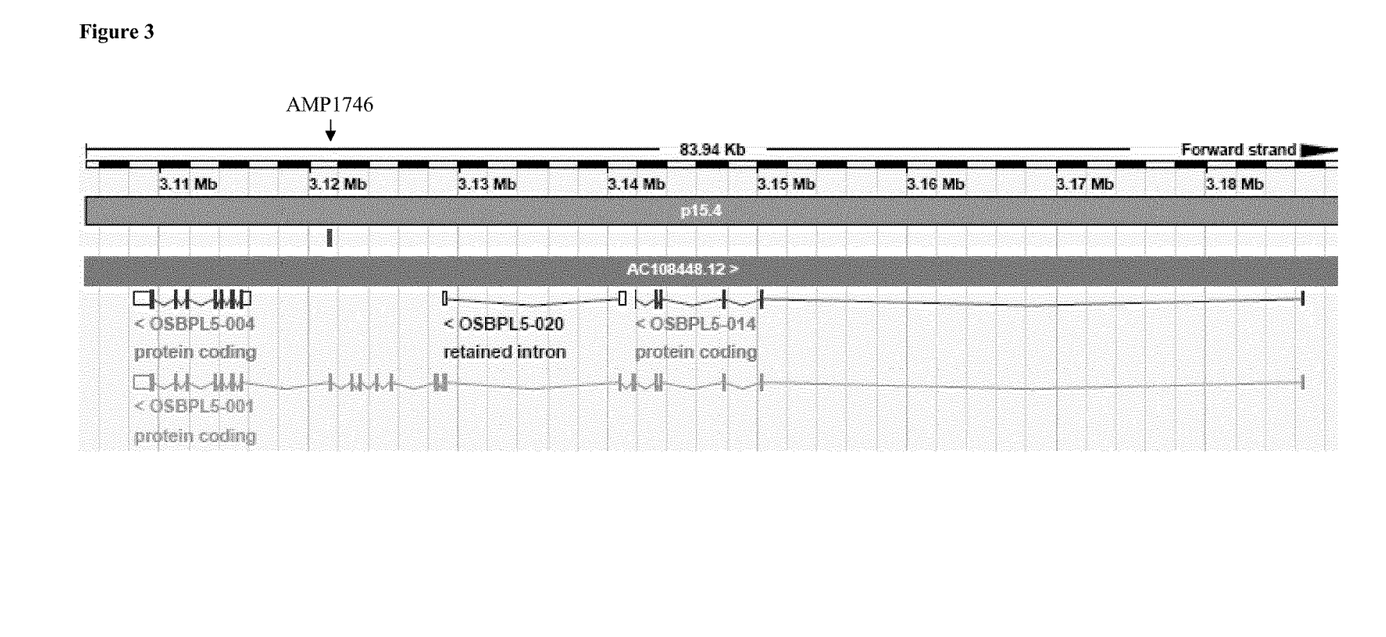
FIG. 3 shows the position of amplicon AMP 1746 (arrow at the top) in the genomic sequence of OSBPL5 (see in particular OSBPL5-001).

Another embodiment of the invention relates to the above methods, wherein said identification comprises a distinction and, optionally, a further quantification, of said natural killer cells from all major peripheral blood cell types or non-blood cells, and then further comprises the step of concluding on the immune status of said mammal based on said natural killer cells as identified. Hereby, in a sample of a mammal, including whole blood or various subfractions as well as tissues or isolated subfractions of tissues, NK cells can be identified and quantified due to their (unique) methylation pattern in the analyzed genes. Based on this they can also be quantitated, as the loss of methylation strictly correlates with NK cells (see, for example, FIG. 2 and table 2).

Herein, the "immune status" of a person shall mean the status of the immune system of a given person in a given situation, in any given tissue type at any given disease situation. For example, it may be important to determine the immune status in a (tumor) tissue biopsy of a person who suffers from a solid tumor. Also, it may be relevant to determine the immune status of a (presumably) healthy person in the peripheral blood in order to determine the persons health status, whereby both an increase or a decrease of the cells—as quantified by the given number of methylated and unmethylated copies of the analyzed genes—may be indicative for a disease, such as for example, the presence of a tumor at an unknown site of the body, or an autoimmune reaction or a chronic infection.

In particular, the inventors regard the herein described methods to be suitable for routine application, for example on a DNA-chip. Samples are selected from a fresh, fresh-frozen or fully prepared (such as formalin fixed paraffin embedded) sample, including mammalian body fluid, preferable human blood samples, (serum samples) or tumorous or non-tumorous solid tissue samples, organ or cell type blood sample. These samples should be mammalian, preferably mouse, rat, monkey, bovine, swine or human. Especially preferred is a mammal, most preferred a human, which suffers from or is likely to suffer from autoimmune diseases, viral or bacterial infections, transplant rejections, cancer including solid and non solid cancers, and/or allergy or any disease directly correlated to NK cells, such as— including but not limited to—diseases as phenotypically described by SCID-X1.

Yet another aspect relates to a method according to the present invention, further comprising the step of concluding on the number and/or amount of said $CD56^{dim}$ natural killer cells as identified in said sample based on said identification and quantification. As the demethylation of the OSBPL genes, particularly in the OSBPL5 gene and the amplicon according to SEQ ID No 1, is so strictly linked to the natural NK cell phenotype (see, for example, table 2), in the most convenient embodiment of said method, the number and/or amount of said natural killer cells (in particular those as defined by CD56+ and/or CD56+ and CD56++) can be correlated directly with the results of the demethylation analysis, if normalized for the copy number in the assay and/or the gender of the subject. In other alternatives, additional control experiments (e.g. demethylated GAPDH analysis in parallel) may be applied.

In a further aspect the inventive method is useful for monitoring the level of $CD56^{dim}$ natural killer cells in a mammal, comprising a method according to the invention, and comparing the amount of natural killer cells as identified to an earlier sample taken from the same mammal, and/or to a control sample.

Yet another aspect relates to a method according to the present invention, further comprising the step of concluding on the immune status of said mammal based on the number and/or amount of said natural killer cells as identified in said sample.

Yet another aspect relates to a method according to the present invention, wherein said mammal suffers from or is likely to suffer from autoimmune diseases, transplant rejections, cancer, infections, allergy and/or any disease directly correlated to NK cells, such as, but not limited to, SCID-X1.

In another aspect of the present invention, the method is also useful for measuring and/or monitoring the amount of said natural killer cells in response to chemical and/or biological substances that are provided to said mammal.

In yet another aspect, the invention provides an amplicon according to SEQ ID NO: 1. The amplicon can be used as a tool in the methods according to the present invention.

The invention also provides a kit for identifying and/or monitoring $CD56^{dim}$ natural killer cells in a mammal based on the analysis of the methylation status of at least one CpG position in one or more of the regions of the gene for oxysterol binding protein-like proteins (OSBPL), in particular for OSBPL5, comprising materials for performing a method according to the invention.

Such an inventive kit preferably comprises, but is not limited to, a) a bisulfite reagent, and b) materials for the methylation analysis of CpG positions selected from the CpG positions of the gene OSBPL5, amplicon 1746 according to SEQ ID NO: 1.

The present invention solves the above problem that the detection of NK cells, in particular $CD56^{dim}$ and $CD56^{bright}$ and $CD16^{low}$ or $CD16^{high}$ NK cells and their distinction from one another, is problematic in essentially all applications in the R&D and in particular in all clinical (routine) applications by providing a method for identifying NK cells of a mammal, comprising analyzing the methylation status of at least one CpG position in one or various, for example regulatory, potentially differentially methylated regions of the genes for OSBPL, such as, for example, OSBPL5, wherein a demethylation, and/or accessibility to bisulfite conversion is highly specific or indicative for $CD56^{dim}$ NK cells ("classical" NK cells).

In another preferred embodiment of the present invention, the inventors furthermore present a novel and more specific way in order to monitor NK cells in all human body fluids, including human whole blood samples, or in any given (solid) tissue, organ or cell type.

The inventive concept is generally based on a specific demethylation and/or accessibility to bisulfite and other chemical base specific conversion of DNA of the OSBPL, such as, for example, OSBPL5, regions in NK cells. Using a simple and precise quantitative PCR method, as a signal amplification method (e.g. a precise quantitative PCR method or other method allowing for the determination of copies of the nucleic acid molecules), the inventors show that the OSPBL, such as OSBPL5, demethylation and/or accessibility to bisulfite conversion represents surrogate markers for lymphocyte counts in blood or tissues. The present inventors have thus identified particular and new regions within the OSPBL, such as OSBPL5, genes that are functionally involved in, or reliably associated with, the existence of natural killer cells.

In one preferred embodiment, the preferred region for this identification is either the promoter, or intron/exon regions of the genes for OSPBL, such as OSBPL5, and other regions containing a number of CpG motifs that exhibit a differential methylation status and/or differential accessibility to bisulfite and other chemical base specific conversion of DNA in cells expressing CD56 in either $CD56^{high}$ or $CD56^{dim}$ cells, which may or may not also express CD16 and CD8 compared with other cells not expressing CD56, using, for example, the bisulphite sequencing method or real time PCR analysis.

The main aspect of the present invention is the distinction between and among functionally different fractions of natural NK cells, namely the cytotoxic sub-fraction (often characterized by the surface markers $CD56^{dim}$, and likely $CD16^{high}$) on one hand and the cytokine producing sub-fraction (i.e., often described as $CD56^{bright}$ and $CD16^{low/medium}$) and other human/animal cell types on the other hand. Alternatively, the method distinguishes between CD8 positive and CD8 negative NK cell fractions or any other sub-fractions of NK cells. While, for the identification of the general NK cell population, a particular preferred embodiment is the identification by the bimodal marker NKG7, the inventors consider the fractionation of the subgroups such as CD8 positive or CD8 negative, the combination of the markers NKG7, CX3CR1, FGR and/or GNLY with the present marker OSPBL, such as OSBPL5, a preferred embodiment. Here, for example, the entire NK population might be typed and quantified by the proportion of NKG7 demethylated cells, while determining the $CD56^{bright}$ or alternatively the $CD56^{dim}$ population by the full demethylation of OSPBL, such as OSBPL5. An implementation example would be that in a sample of full blood, the number of cells with an unmethylated NKG7 region determines the absolute number of NK-like cells, while the number of OSPBL, such as OSBPL5, demethylated cells determines the proportion of the $CD56^{dim}$ population. In such setting and as one embodiment, using the demethylation of OSPBL, such as OSBPL5, alone would provide for the identification of the $CD56^{dim}$ population only, without determining the amount of the other NK or other cell fractions.

The inventors could demonstrate that in all $CD56^{dim}$NK cells the CpG motifs are almost completely demethylated (i.e. to more than 70%, preferably 80%, preferably, more than 90% and most preferred more than 95%, see above), whereas the same motifs are completely methylated in all non-NK and non-$CD56^{dim}$NK cells. Determination of the methylation status of the OSPBL, such as OSBPL5, loci is therefore a valuable tool to identify NK cells, such as will be required/or at least of some value for measuring NK cells in autoimmune diseases, (viral) infections, transplant rejections, cancer, infections, allergy, or just the NK cell related immune status in any envisionable context, when desired. The assay allows measurement of NK cells without purification or any staining procedures. As a particularly preferred embodiment, the measurement of NK cells by either of the markers described in here can be easily detected and quantified from within solid tissue samples of healthy or diseased nature, including tumorous or non-tumourous tissues. For such analysis it is possible to make the analysis either from fresh, fresh-frozen or any type of conserved (such as, for example, formalin fixed and/or paraffin-embedded) tissue. Another preferred embodiment is to determine the ratio between NK cells on one hand and CD3+ T lymphocytes, CD19 positive B cells, FOXP3 CD25 CD3+ cells, monocytes and/or granulocytes on the other, as well as $CD56^{dim}$ NK cells versus $CD56^{bright}$, $CD56^{dim}$ NK cells versus all lymphocytes, $CD56^{dim}$ NK cells versus all leukocytes, or $CD56^{dim}$ NK cells versus all cytotoxic cells.

The inventors have shown that the potential to form NK cell properties of mammalian immune cells coincide with epigenetic, i.e., DNA methylation based regulation in the genes for OSPBL, such as OSBPL5. DNA methylation is a biologically and chemically stable epigenetic modification, resulting in long-term gene expression changes. The inventors found demethylation and/or the accessibility of the genomic DNA to bisulfite conversion at the human OSBPL5 locus to be restricted to $CD56^{dim}$ NK cells when tested against all major peripheral blood cell types and a selection of different non-blood cell types/lines. These data indicated that epigenetic modifications in the OSPBL loci, such as the OSBPL5 locus, serve as valuable marker for the identification of cells with the phenotype of NK cells, regardless of the expression of any genes.

The present invention relies on the surprising finding that in a particular region of the gene for OSBPL5, a so-called "NK-SDR"s (NK cell specific demethylated regions), the CpG motifs are almost completely demethylated to more than 70%, preferably more than 80%, more preferably to more than 90%, preferably 91%, even more preferably more than 92% and most preferred more than 95%, whereas the same motifs are completely methylated in all non NK cells (see above). Thus, this region provides a valuable and reliable tool for a diagnostic analysis according to the present invention.

It is well established in the art that often additional and important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention, NK-SDRs are provided, which are located within 10000 bases upstream of the transcriptional start site of OSBPL5, preferably 9000 bases, 8000 bases, 7000 bases, 6000 bases, 5000 bases, 4000 bases, 3000 bases or 2000 bases upstream of OSBPL5, even more preferred is a region 1000 bases upstream of the transcriptional start of OSBPL5 and most preferable NK-SDRs in the first 500 bases upstream of the transcriptional start site of OSBPL5. It is, however, particularly preferred that NK-SDRs of the present invention are located within the gene promoter of OSBPL5.

Moreover, additional preferred embodiments of the present invention comprise NK-SDRs downstream of the open reading frame (ORF) of OSBPL5, preferably within 10000 bases downstream of the ORF of OSBPL5, more preferable 8000 bases downstream of OSBPL5, even more preferred is a region 6000 bases downstream of the ORF of OSBPL5, preferably 4000 bases downstream of OSBPL5 and most preferable NK-SDRs in the first 2000 bases downstream of the ORF of OSBPL5.

The present invention further preferably provides groups of NK-SDRs of OSBPL5, which comprise any possible combination of the aforementioned preferred NK-SDRs of OSBPL5 and the region as described, for example, in SEQ ID No. 1, above.

The gene NKG7 in humans is located on the reverse strand of chromosome 19. The gene region spans roughly 1.3 kb comprising 5' and 3' UTRs, 4 exons and 3 intronic regions (Ensembl release 53, March 2009). There is only evidence for a single splice variant of the gene, a mature transcript of 826 nucleotides which encodes for 165 amino acids of the final NKG7 protein product. In a further aspect, a preferred NK-SDR is the 5' UTR of NKG7, or preferable the 3' UTR of NKG7. Furthermore, natural killer cell specific demethylated regions of the present invention are located within the intronic sequences of this gene. In particular preferred are also NK-SDRs that are located around the exon-intron boundaries of NKG7, preferably the boundary between the first exon and first intron and/or the first intron and second exon and/or the second exon and second intron and/or the second intron and third exon and/or the third exon and third intron and/or the third intron and fourth exon, or any possible preferred combination of the above.

The gene CX3CR1 in humans is located on the reverse strand of chromosome 3. The gene region spans roughly 18.5 kb genomic DNA comprising 5' and 3' UTRs, 3 exons and 2 intronic regions (Ensembl release 53, March 2009). There are three alternatively spliced variants of the transcript that encode for final protein products ranging in size between 355 to 387 amino acids. In a further aspect, a preferred NK-SDR is the 5' UTR of CX3CR1, or preferable the 3' UTR of CX3CR1. Furthermore, natural killer cell specific demethylated regions of the present invention are located within the intronic sequences of this gene. In particular preferred are also NK-SDRs that are located around the exon-intron boundaries of CX3CR1, preferably the boundary between the first exon and first intron and/or the first intron and second exon and/or the second exon and the second intron and/or the second intron and third exon, or any possible preferred combination of the above.

In another embodiment, the method according to the present invention is preferred, wherein said analysis of the methylation status comprises amplification with at least one primer of the primer pairs useful to amplify the amplicon according to SEQ ID NO: 1.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, sequencing or methyl specific restriction assays. With the amplification, the amplicon of the NK-SDR or any other region in the OSPBL, such as OSBPL5, genes or any paralog or ortholog as described herein is produced that is a particularly preferred "tool" for performing the method(s) according to the present invention. Consequently, a primer pair for the amplification of the regions according to SEQ ID NO: 1 or SEQ ID NO: 2 and parts thereof constitutes a preferred embodiment of the present invention.

Furthermore, preferred is a method according to the invention, further comprising the step of analyzing the cellular markers CD56, CD16 and/or CD8. In order to analyze these additional markers, any known method to analyze expression can be used, such as methods using antibodies, and/or methylation analysis. The analysis of these markers preferably further improves the accuracy of the analysis, and might allow to identify sub-sets of cells. Thus, the method according to the present invention comprises an identification that is a distinction of said natural killer cells from all major peripheral blood cell types or non-blood cells.

The method according to the present invention can be performed with any mammal having the above markers or orthologs or paralogs thereof, preferred is a method according to the present invention, wherein said mammal is a mouse, rat, pig or cow, monkey or human, preferably a human.

The method(s) according to the present invention can be performed in vitro and/or in vivo. In general, all biological samples can be used, as long as they contain suitable cells or suitable DNA of cells of interest. Preferred is a method wherein said sample is selected from a fresh, fresh-frozen or fully prepared sample including mammalian body fluid, preferable human whole blood samples, serum samples or a tumorous or non-tumorous solid tissue, organ or cell type blood sample, a sample of blood lymphocytes or a fraction thereof.

Another preferred aspect of the present invention then relates to the use of the method according to the present invention as above in diagnostics and the use in monitoring diseases. Thereby, in an alternative embodiment, the invention is directed at a method according to the present invention which further comprises the step of concluding on the immune status of said mammal based on said natural killer cells as identified. In said method according to the invention, a demethylation of at least one CpG position in a first gene selected from OSPBL, such as OSBPL5, optionally in combination with a demethylation of at least one CpG position in at least a second gene selected from, for example, NKG7, CX3CR1, FGR, and GNLY, is indicative for a $CD56^{dim}$ or $CD56^{bright}$ natural killer cell.

Another important aspect of the present invention then relates to a method according to the present invention for monitoring the level of CD56 expressing natural killer cells, in particular $CD56^{dim}$ or $CD56^{bright}$, and/or $CD16^+$ or $CD16^-$, and/or $CD8^+$ or $CD8^-$ natural killer cells in a mammal, comprising a method according to the invention as above, and comparing the amount of natural killer cells as identified with an earlier sample taken from the same mammal, and/or with a control sample. Preferably, said method is performed on a sample from a mammal suffering from or is likely to suffer from autoimmune diseases, transplant rejections, cancer, infection, allergy and/or any disease directly correlated to NK cells, such as, but not limited to SCID-X1.

Further preferred, said method according to the invention then further comprises measuring and/or monitoring the amount of the amount of natural killer cells in response to chemical and/or biological substances that are provided to said mammal. That is, changes in the amount or ratio of natural killer cells that are caused by, for example, the treatment of a disease (e.g. as described herein), and the success and/or progress of said treatment in terms of an effect on the natural killer cells can be followed using this method. A follow-up of the methylation pattern based on the markers herein will point to changes in the cells that are due to a response to said chemical and/or biological substances, in some cases even before a phenotypic change can be observed.

In yet another aspect of the present invention, the present invention provides a method for identifying chemical and/or biological substances that selectively modulate natural killer cells expressing the markers as described herein, comprising contacting one or more of said chemical and/or biological substance with said natural killer cells, and detecting, whether said chemical and/or biological substance modulates the methylation of the CpG positions as analyzed, and/or whether said one or more of said chemical and/or biological substance selectively modulates the amount and/or ratio of marker-expressing natural killer cells. Particularly preferred is a modulation of said natural killer cells that increases the amount and/or ratio of said natural killer cells.

The method can be performed in vitro and/or in a suitable animal. In this aspect, the present invention provides a method, sometimes called a "screening-method", that seeks to identify chemical and/or biological substances modulating expression of the markers as above that can be used as starting points for the development of natural killer cell-specific medication and respective pharmaceutical compositions. The present method is based on the fact that it is well accepted that the marker genes as identified herein must play a central role for the development of natural killer cells. Therefore, factors stimulating marker expression are interesting for the treatment of patients. Such factors, which lead to a stable modification, preferably induction, of the development/ratio/amount of natural killer cells, can be detected with the method described in this invention.

Chemical and/or biological substances that are suitable as screening compounds are known to the person of skill and, for example, include small molecules, peptides and proteins, and antibodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 80%, preferably 90%, and more preferably 95%.

Another important aspect of the present invention then relates to a method according to the present invention, which further comprises the step of providing a treatment for a patient suffering from or being likely to suffer from autoimmune diseases, transplant rejections, cancer, allergy and/or any disease directly correlated to NK cells, such as, but not limited to SCID-X1, wherein said treatment modulates, and preferably increases the amount and/or proportion of NK cells in said, preferably, cancer patient. Preferred is a method according to the present invention, wherein said treatment is selected from providing chemical and/or biological substances that selectively stimulate NK cells in said patient, or a treatment that stimulates the expression of the marker genes as above or supports the biological activity of said marker genes in said NK cells in said patient. Preferred examples of such treatments are demethylating agents that provide for a reduced methylation of said genes. Other preferred examples of such treatments are agents that provide for a reduced number of NK-cells in case of autoimmune diseases.

Yet another preferred aspect of the present invention relates to an improved method of treatment of diseases that are related to marker gene expression and/or demethylation, such as autoimmune diseases, transplant rejections, cancer, allergy and/or any disease directly correlated to NK cells, such as, but not limited to SCID-X1, comprising a method as described herein above. The term "treatment" also includes a prevention of marker gene expression and/or demethylation related diseases.

In yet another aspect of the present invention, the present invention relates to the use of an amplicon according to the present invention or a kit according to the present invention for identifying and/or monitoring $CD56^{dim}$ natural killer cells in a mammal and/or $CD56^{bright}$ and/or $CD16^+$ or $CD16^-$, and/or $CD8^+$ or $CD8^-$ natural killer cells in a mammal.

The present invention will now be further described in more detail in the form of preferred embodiments thereof in the following examples, nevertheless, without being limited thereto. For the purposes of the present invention, all references as cited herein are incorporated by reference in their entireties.

SEQ ID NO: 1 shows the nucleotide sequence of AMP 1746;

SEQ ID NO: 2 shows the nucleotide sequence of the human genomic region around AMP 1746;

SEQ ID NOs: 3 and 4 show the nucleotide sequence of the TpG and CpG specific oligos as used in the examples; and SEQ ID NO: 5 shows the nucleotide sequence of the TaqMan-probe as used in the examples.

EXAMPLES

Example 1

The inventors have purified various blood subsets including CD3/CD4, CD3/CD8 naïve and memory T lymphocytes, various different fractions of CD56 natural killer cells, such as NKT $CD3^-CD56^+$, $CD3^-CD56^+$, $CD3^-CD56^{++}$, as well as CD19 naïve and memory B cells, CD14 monocytes, CD15 granulocytes, as well as non lymphogenic cell lines (see table 1). DNA from the purified cells was bisulfite-treated analyzed at various CpG dinucleotide motifs. The inventors then compared the methylation status (finding C as for Cytosine that was methylated in the original (genomic) sequence versus T for cytosine that was unmethylated in the original sequence).

Surprisingly, it was found that specific areas in the genomic regions of the genes for OSBPL, and particularly of OSBPL5 are significantly demethylated in natural killer cells compared to any other cell type, as can be seen in the following table 1.

TABLE 1

PCR analysis in different blood cell subtypes and different cell lines

| Analyzed Samples Customer-ID | PCR-System specific to "TpG" | | | PCR-System specific to "CpG" | | | NK [%] | Cell type |
|---|---|---|---|---|---|---|---|---|
| | CP Value | Plasmid units | S.D. | CP Value | Plasmid units | S.D. | | |
| CD8 | 32.6 | 54.0 | 23.1 | 25.6 | 3493.3 | 64.3 | 1.5 | CD8 |
| CD8 | 32.8 | 32.5 | 15.5 | 26.0 | 2663.3 | 11.5 | 1.2 | |
| CD4 memory | ND | ND | ND | 25.9 | 2766.7 | 40.4 | ND | CD4 |
| CD4 naive | ND | ND | ND | 25.9 | 2866.7 | 11.5 | ND | |
| CD4+ total | 35.53 | 4.35 | 0.52 | 25.7 | 6050.12 | 0.02 | 0.07 | |
| Monocytes | 34.2 | 0.3 | 0.2 | 27.2 | 1150.0 | 40.0 | 0.0 | MOC |
| Monocytes | 34.3 | 2.9 | 4.7 | 25.8 | 3113.3 | 135.0 | 0.1 | |
| Monocytes | 33.6 | 3.7 | 3.9 | 25.4 | 3850.0 | 104.4 | 0.1 | |
| Granulocytes | 34.3 | 0.1 | ND | 24.4 | 7886.3 | 595.3 | 0.0 | GRC |
| Granulocytes | 34.3 | 0.1 | ND | 24.7 | 6630.0 | 334.2 | 0.0 | |
| Granulocytes | 33.7 | 2.3 | 1.3 | 22.3 | 33166.7 | 2203.0 | 0.0 | |
| B cells | ND | ND | ND | 26.5 | 1863.3 | 60.3 | ND | B |
| B cells | 34.6 | 0.1 | 0.2 | 28.8 | 378.7 | 29.9 | 0.0 | |
| B cells | 34.6 | 0.0 | ND | 25.5 | 3640.0 | 157.2 | 0.0 | |
| CD3− CD56++ CD16− NKbright | ND | ND | ND | ND | ND | ND | ND | NK bright |
| CD3− CD56++ CD16− NKbright | 34.4 | 0.8 | 1.3 | 28.2 | 576.3 | 31.6 | 0.1 | |
| CD3− CD56++ CD16− NKbright | 35.0 | 0.0 | 0.0 | 28.6 | 428.3 | 24.1 | 0.0 | |
| NK classic CD3− CD56+ CD16+ | 28.9 | 1256.7 | 194.3 | 30.6 | 109.4 | 23.0 | 92.0 | NK classic |
| NK classic CD3− CD56+ CD16+ | 27.8 | 2376.7 | 96.1 | 28.7 | 401.7 | 13.8 | 85.5 | |
| NK like CD8+ | 33.1 | 15.2 | 9.9 | 28.1 | 627.0 | 40.0 | 2.4 | NKT |
| NK like CD8+ | 34.2 | 0.6 | 0.5 | 34.1 | 14.4 | 3.9 | 4.0 | CD8+ |
| CD56 depleted CD8 | 32.0 | 150.8 | 61.6 | 25.7 | 3240.0 | 98.5 | 4.4 | CD56 depleted CD8 |
| CD8 naive CD8+ CD45RA+ CCR7+ | 34.1 | 0.3 | ND | 26.2 | 2353.3 | 65.1 | 0.0 | CD8 naive |
| CD8 naive CD8+ CD45RA+ CCR7+ | ND | ND | ND | 30.0 | 171.7 | 4.2 | ND | |
| CD8 naive CD8+ CD45RA+ CCR7+ | ND | ND | ND | 26.5 | 1840.0 | 34.6 | ND | |
| CD8 effector memory | 34.1 | 0.4 | ND | 27.2 | 1153.3 | 28.9 | 0.0 | CD8 eff memory |
| CD8 effector memory | ND | ND | ND | 30.1 | 161.0 | 15.1 | ND | |
| CD8 effector memory | ND | ND | ND | 25.6 | 3420.0 | 95.4 | ND | |
| keratinocytes | ND | ND | ND | 26.0 | 2213.3 | 2.9 | ND | Cell lines |
| cartilage | 31.9 | 66.4 | 3.0 | 23.9 | 9280.0 | 1.5 | 0.7 | |
| osteogenic activated MSC | 36.8 | 1.9 | ND | 27.8 | 598.3 | 1.8 | 0.3 | |
| chondrogenic activated MSC | 34.2 | 13.4 | 49.9 | 25.8 | 2523.3 | 2.5 | 0.5 | |
| lung carcinoma cell line | ND | ND | ND | 25.5 | 3003.3 | 1.8 | ND | |

The data shows various CpG sites and motifs in regions in the OSBPL5 gene that were demethylated in then NK classic CD3−CD56+CD16+ cell samples, while fully methylated in all other blood cell types, such as, for example, CD56++ cells.

Figure 1:
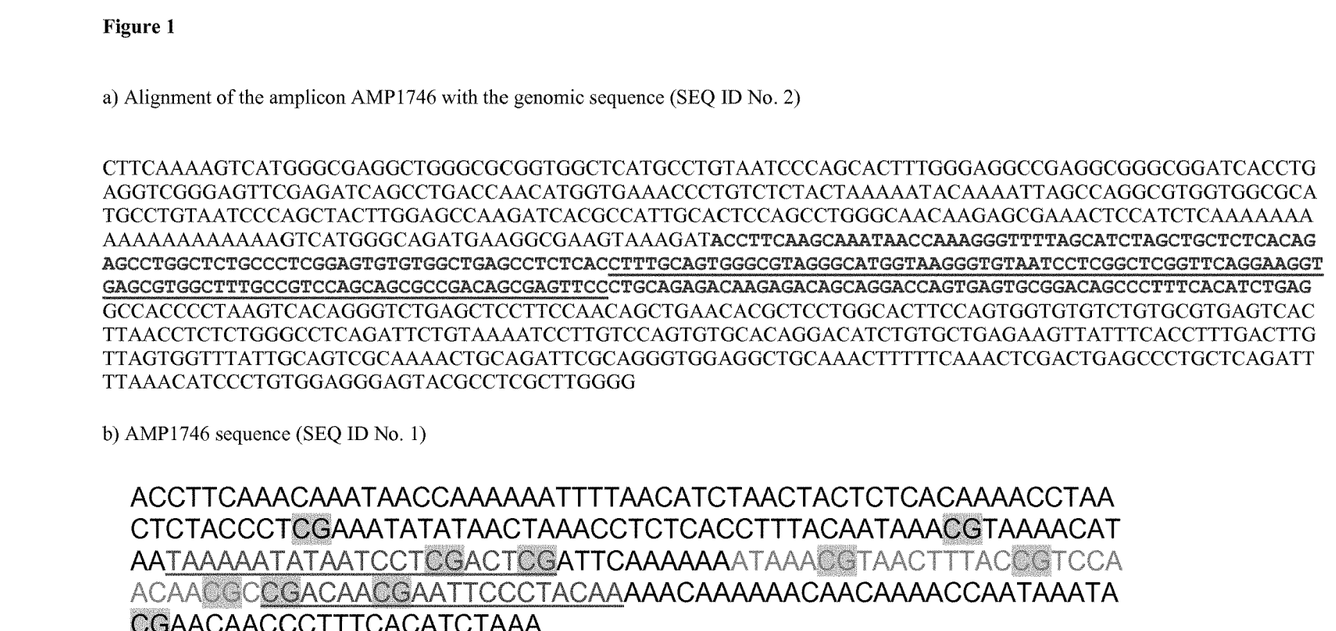
FIG. 1 shows a) the alignment of amplicon AMP 1746 (bold) in the genomic sequence. Furthermore, exon 14 of OSBPL5 is underlined. Thus, exon 14 is smaller than AMP1746 which therefore also covers the 5' as well as the 3' intron/exon border of exon 14, and b) the sequence of the amplicon AMP 1746 (SEQ ID No. 1) as well as CpGs (shaded), TpG and CpG-specific oligos (underlined), and the Taqman probe (gray nucleotides).

Then, upon finding of the differential methylation, the inventors analyzed larger genomic regions by means of bisulfite sequencing. This latter procedure served for exploring and extending the differentially methylated regions and was conducted, for example with the differentially methylated gene regions of OSBPL5 as shown in FIG. 1.

Example 2

In this experiment the specificity, robustness, and accuracy of the assay according to the present invention was tested in a spiking assay with granulocyte DNA. It was found that the assay identified the NK cell-DNA with high specificity and accuracy over most of the range as analyzed (0.625% to 20% DNA) as shown in table 2.

TABLE 2

PCR analysis: spiking of NK cell DNA in granulocyte DNA

| Analyzed Samples | | PCR-System specific to "TpG" | | | PCR-System specific to "CpG" | | | NK [%] |
|---|---|---|---|---|---|---|---|---|
| Epionts- ID | Cust-omer- ID | CP Value | Plasmid units | C.V. (%) | CP Value | Plasmid units | C.V. (%) | |
| NKC07- 20% | | 28.73 | 722.33 | 1.97 | 25.01 | 3573.33 | 3.72 | 16.82 |
| NKC07- 10% | | 29.67 | 383.00 | 4.84 | 24.74 | 4296.67 | 1.42 | 8.18 |
| NKC07- 5% | | 30.77 | 182.67 | 6.39 | 24.78 | 4190.00 | 5.70 | 4.18 |
| NKC07- 2.5% | | 31.89 | 85.63 | 11.98 | 24.80 | 4116.67 | 6.06 | 2.04 |
| NKC07- 1.25% | | 32.69 | 49.67 | 13.52 | 24.86 | 3970.00 | 1.33 | 1.24 |
| NKC07- 0.625% | | 33.89 | 11.84 | 50.39 | 24.65 | 4563.33 | 0.13 | 0.26 |
| GRC12 | | ND | ND | ND | 24.72 | 4346.67 | 1.96 | ND |

The invention claimed is:

1. A method for quantifying classical cytotoxic natural killer cells (NK cells) in a sample derived from a human, comprising analyzing the methylation status of at least one CpG position in the genomic sequence of SEQ ID NO: 1, the method comprising:
   a) obtaining from the human a sample that contains NK cells;
   b) isolating DNA from the sample;
   c) treating the DNA with bisulfite;
   d) amplifying bisulfite treated DNA from step c) using a quantitative PCR system comprising a TpG specific primer pair of SEQ ID NOS 3 and 4;
   e) quantifying the amplicons from step d) with a TpG specific probe of SEQ ID NO: 5;
   f) amplifying bisulfite treated DNA from step c) using a quantitative PCR system comprising a CpG specific primer pair of SEQ ID NOS: 3 and 4;
   g) quantifying the amplicons from step f) with a CpG specific probe of SEQ ID NO: 5; and
   h) quantifying the classical cytotoxic NK cells based on the quantity of amplicons determined in step e) compared to the quantity of amplicons determined in step e) and step g).

2. The method according to claim 1, wherein at least one CpG position is selected from CpG positions 130, 135, 152, 163, 173, 176, or 182 of SEQ ID NO:1.

3. The method according to claim 1, wherein the quantity of amplicons produced using the TpG-specific primers is more than 70% of the quantity of amplicons produced using the TpG-specific and CpG-specific primers.

4. The method according to claim 1, further comprising analyzing the markers CD56, CD16, and/or CD8.

5. The method according to claim 1, further comprising distinguishing said classical cytotoxic natural killer cells from peripheral blood cell types, non blood cells, and/or CD56$^{bright}$ cells.

6. The method according to claim 1, wherein said sample is a blood sample or a tissue sample.

7. The method according to claim 1, further comprising the step of determining the immune status of said human based on the quantity of classical cytotoxic natural killer cells in said sample.

8. A method for monitoring the level of classical cytotoxic natural killer cells in a human, comprising performing the method of claim 1 and comparing the quantity of classical cytotoxic natural killer cells with an earlier sample taken from the same human, and/or with a control sample.

9. The method according to claim 1, wherein said human suffers from or is likely to suffer from an autoimmune disease, transplant rejection, cancer, infection, allergy and/or any disease directly correlated to NK cells.

10. The method of claim 1 further comprising providing a chemical and/or biological substance to the human prior to step a) and measuring the quantity of said classical cytotoxic natural killer cells in the sample.

11. The method, according to claim 3, wherein at least 95% of the amplicons are produced using the TpG-specific PCR system.

12. The method, according to claim 9, wherein said human suffers from SCID X1.

* * * * *